(12) United States Patent
Kim et al.

(10) Patent No.: US 12,318,462 B2
(45) Date of Patent: Jun. 3, 2025

(54) MULTI-COATED NANOPARTICLES COMPRISING MULTIPLE COATING LAYERS OF CHITOSAN AND POLYGLUTAMIC ACID, COMPOSITION FOR SKIN CARE COMPRISING THE SAME AND METHOD FOR MANUFACTURING THE SAME

(71) Applicant: BINOTEC co., ltd., Daegu (KR)

(72) Inventors: Yu-Mi Kim, Daegu (KR); Gi-Hyun Jang, Daegu (KR)

(73) Assignee: BINOTEC CO., LTD., Daegu (KR)

( * ) Notice: Subject to any disclaimer, the term of this patent is extended or adjusted under 35 U.S.C. 154(b) by 0 days.

(21) Appl. No.: 17/318,339

(22) Filed: May 12, 2021

(65) Prior Publication Data

US 2022/0133604 A1    May 5, 2022

(30) Foreign Application Priority Data

Nov. 5, 2020   (KR) .......................... 10-2020-0147085

(51) Int. Cl.
| | | |
|---|---|---|
| A61K 8/14 | (2006.01) | |
| A61Q 19/00 | (2006.01) | |
| B82Y 5/00 | (2011.01) | |
| B82Y 30/00 | (2011.01) | |
| B82Y 40/00 | (2011.01) | |

(52) U.S. Cl.
CPC ............... *A61K 8/14* (2013.01); *A61Q 19/00* (2013.01); *A61K 2800/413* (2013.01); *A61K 2800/614* (2013.01); *A61K 2800/63* (2013.01); *A61K 2800/654* (2013.01); *A61K 2800/805* (2013.01); *B82Y 5/00* (2013.01); *B82Y 30/00* (2013.01); *B82Y 40/00* (2013.01)

(58) Field of Classification Search
None
See application file for complete search history.

(56) References Cited

FOREIGN PATENT DOCUMENTS

| KR | 10-1810160 | 1/2018 | |
|---|---|---|---|
| WO | 2019-004563 | 1/2019 | |
| WO | WO-2019004563 A1 * | 1/2019 | ............... A61K 8/14 |

OTHER PUBLICATIONS

Stadler et al.; "Capsosomes: Subcompartmentalizing Polyelectrolyte Capsues Using Liposomes," 2009; ACS-Publishing; Langmuir, vol. 25, No. 12, pp. 6725-6732. (Year: 2009).*

Yaroslavov et al.; "Polyelectrolyte-coated liposomes: Stabilization of the interfacial complexes," 2008, Elsevier; Advances in Colloid and Interface Science, vol. 142, pp. 43-52. (Year: 2008).*
Lee et al. ("Improving solubility, stability, and cellular uptake of reseveratrol by nanoencapsulation with chitosan and γ-poly(glutamic acid)," 2016; Elsevier; Colloids and Surfaces B: Biointerfaces, vol. 147, pp. 224-233. (Year: 2016).*
Kim et al.; "Transformer-ethosomes with palmitoyl pentapeptide for improved transdermal delivery," 2019, Elsevier; Journal of Drug Delivery Science and Technology, vol. 52, pp. 460-467. (Year: 2019).*
Jeon et al.; "Improved stability and skin permeability of sodium hyaluronate-chitosan multilayered liposomes by layer-by-layer electrostatic deposition for quercetin delivery," 2015, Elsevier; Colloids and Surfaces B: Biointerfaces, vol. 129, pp. 7-14. (Year: 2015).*
Antunes et al.; "Layer-by-Layer Self-Assembly of Chitosan and Poly(γ-glutamic acid) into Polyelectrolyte Complexes," 2011; ACS; Biomacromolecules, vol. 12, pp. 4183-4195. (Year: 2011).*
Song et al.; "Layer-by-Layer Build up of Poly(L-glutamic acid)/Chitosan Film for Biologically Active Coating," 2009, Wiley-VCH; Macromolecular Bioscience, vol. 9, pp. 268-278. (Year: 2009).*
Endmemo; retrieved from www.endmemo.com/sconvert/mg_mlper. php on Jan. 5, 2023, p. 1. (Year: 2023).*
Florence Hermal et al.,"Development and characterization of layer-by-layer coated liposomes with poly(L-lysine) and poly(L-glutamic acid) to increase their resistance in biological media", International Journal of Pharmaceutics, Elsevier, NL, vol. 586, Jun. 24, 2020, XP086242279.
Weilin Liu et al., "Multilayered vitamin C nanoliposomes by self-assembly of alginate and chitosan: Long-term stability and feasibility application in mandarin juice", LWT-Food Science and Technology, Academic Press, UK, vol. 75, Oct. 6, 2016, p. 608-615, XP029788256.
EPO, Supplementary European Search Report of the corresponding European Patent Application No. 21188030.7., dated Feb. 2, 2022.
Ai-jun Shen et al., "Polyelectrolyte layer-by-layer assembled lipid nanoparticles for improving oral absorption of doxorubicin", Yao Xue Xue Bao, 2016, 51(7), pp. 1136-1143. (abstract only).

* cited by examiner

*Primary Examiner* — Tigabu Kassa
*Assistant Examiner* — Ivan A Greene
(74) *Attorney, Agent, or Firm* — LEX IP MEISTER, PLLC

(57) ABSTRACT

Multi-coated nanoparticles including multiple coating layers of chitosan and polyglutamic acid, composition for skin care including the same, and method of manufacturing the same are provided. The nanoparticles have a liposome core layer and coating layers. The core layer includes a bioactive particle and a core hydrogel. Not only is it easy to mass-produce, but also has the effect of steadily releasing bioactive particles for a long period of time due to its high sealing rate and high stability.

12 Claims, 6 Drawing Sheets

MULTI-COATED NANOPARTICLES COMPRISING MULTIPLE COATING LAYERS OF CHITOSAN AND POLYGLUTAMIC ACID, COMPOSITION FOR SKIN CARE COMPRISING THE SAME AND METHOD FOR MANUFACTURING THE SAME

CROSS-REFERENCE TO RELATED APPLICATION

This application claims priority to and benefits of Korean Patent Application No. 10-2020-0147085, filed in the Korean Intellectual Property Office on Nov. 5, 2020, the entire amounts of which are incorporated herein by reference.

BACKGROUND

(a) Field

The present invention relates to multi-coated nanoparticles including multiple coating layers, composition for skin care comprising the same and a method of manufacturing the same.

(b) Description of the Related Art

Liposomes, similar to cell membranes, are drug delivery systems that contain a double lipid membrane and can entrap a bioactive substance. Liposomes have been widely used in pharmaceuticals and cosmetics because they have high biocompatibility and can deliver various active substances in vivo.

The nanoparticle carrier has a high skin absorption rate. However, the nanoparticle delivery system is difficult to control the initial release of the drug enclosed therein, and the physical stability is low. Therefore, there is a limitation in that the drug enclosed inside is easily released. In order to overcome this limitation, studies to induce sustained release of nanoparticles in various ways have been conducted.

In studies inducing sustained-release of nanoparticles, multi-layer liposomes are generally used. However, the entrapment efficiency of the nano-liposome formed with a multi-layer of phospholipids was low, from 60 to 70%, and there was a disadvantage in that the stability was maintained for only one week.

Chitosan has excellent biocompatibility and biodegradability. Chitosan is not toxic to the human body and is hydrolyzed in vivo by specific enzymes. Since chitosan is a cationic hydrogel, it exerts strong electrostatic force on anionic liposomes to form a film. As a result, chitosan can be used for sustained-release studies. However, it is difficult to obtain stability suitable for commercialization of nanoparticles in which chitosan is primary coated on liposomes.

The above information disclosed in this Background section is only for enhancement of understanding of the background of the invention, and therefore, it may contain information that does not form the prior art that is already known in this country to a person of ordinary skill in the art.

SUMMARY

An active ingredient is entrapped in a nano-liposome, and chitosan and polyglutamic acid are alternately coated on the surface of a nano-liposome to provide a multi-coated nanoparticle. In addition, composition for skin care including the multi-coated nanoparticle is provided. The composition for skin care can be used as cosmetics or therapeutic agent. These nanoparticles have high entrapment efficiency and stability of bioactive substances, and effectively release drugs in a sustained-release manner. In particular, the multi-coated nanoparticles can control the concentration of the hydrogel, and the particle charge moves toward the neutral side. Therefore, nanoparticles can be developed as a drug delivery system that is friendlier to the living body.

The multi-coated nanoparticles according to an embodiment of the present invention include bioactive particles, core hydrogels, and phospholipids, and include a core layer with a liposome structure. The multi-coated nanoparticles include a first coating layer including chitosan; a second coating layer including polyglutamic acid; and a third coating layer including chitosan.

A method for manufacturing a multi-coated nanoparticle according to an embodiment of the present invention includes forming a core layer by mixing a phospholipid in a solution including a bioactive particle and a core hydrogel to form a liposome; first coating chitosan on the core layer; second coating polyglutamic acid on the first coating layer; and a third coating chitosan on the second coating layer.

A multi-coated nanoparticle according to an embodiment of the present invention includes a core layer with a liposome structure. The core layer includes bioactive particles, core hydrogels, and phospholipids. The multi-coated nanoparticle includes a first coating layer including chitosan; a secondary coating layer including polyglutamic acid; and a third coating layer including chitosan.

The nanoparticles may have a multi-layer structure including a core layer and multi-layers. The multi-layers may have at least two coating layers. Coating means that a layer is formed on the outside of an existing structure through electrostatic bonding. The coating can be distinguished from the particulate structure by simple electrostatic bonding.

The core layer means a body located at the center of the nanoparticle. The core layer includes a hydrogel and a bioactive substance, and may further include a phospholipid layer.

The hydrogel means a gel in which a crosslinked polymer matrix is partially or completely swollen with water, one or more water-compatible alcohols, or combinations thereof. Thus, the hydrogel may include an alcogel that has been partially or completely swollen with a water-compatible alcohol. The crosslinking of the polymer matrix may be chemical or physical crosslinking. For example, hydrogels can be crosslinked through covalent bonds, ionic interactions, hydrogen bonding, chain entanglement, or self-association of microphase segregating moieties.

The core hydrogel may have a charge opposite to that of the bioactive particles. The core hydrogel can electrostatically bind to the bioactive particles of the nanoparticles, thereby lowering the drug release rate of the nanoparticles and increasing the stability.

Hydrogel may be at least one substance selected from a group of hyaluronic acid, alginate, pectin, carrageenan, dextran sulfate, guar gum, gum arabic, xanthan gum, polyacrylic acid, polygalaturonic acid, carboxymethylcellulose, polyglutamic acid (PGA) carbomer, agar, collagen peptide, starch, hydrolyzed starch, crosslinked starch, modified starch, dextrin, gamma polyglutamic acid, gelatin, alginic acid, and chitosan.

Bioactive particle means a therapeutically active agent capable of providing a direct or indirect, therapeutic, physiological and/or pharmacological effect on a human or animal organism. The therapeutically active agent may be a water-soluble bioactive substance or a medicinal bioactive substance. The therapeutically active agent is a general medicine, a drug, a prodrug or a target group, or a drug including a target group, a prodrug, a cosmetic composition, a substance that affects the regulation of the physiological activity of the skin, a food supplement that can benefit health, or a composition of health functional food.

The bioactive particle may be one or more substances selected from the group consisting of peptides, natural extracts, and vitamins. The therapeutically active agent can be at least one substance selected from a group of coenzyme Q10 (ubiquinone), ubiquinol or resveratrol; carotenoids such as α, β or γ-carotene, lycopene, lutein, zeaxanthin and astaxanthin; phytonutrients such as lycopene, lutein or cyanoxanthin; Omega-3 fatty acids including linoleic acid, conjugated linoleic acid, docosahexaenoic acid (DHA), erycosapentaenoic acid (EPA) or their glycerol-esters; Vitamin D (D2, D3 and derivatives thereof), vitamin E (α, β, γ, δ-tocopherol, or α, β, γ, δ-tocotrienol), vitamin A (retinol, retinal, retinoic acid and derivatives), Fat-soluble vitamins including vitamin K (K1, K2, K3 and derivatives thereof), capric/caprylic triglycerides, folic acid, iron, niacin, glyceryl linoleate, omega 6 fatty acids, vitamin F, selenium, cyanocobalamin, Aloe vera, beta glucan, bisabolol, *Camellia thea* (green tea) extract, capric/caprylic triglyceride, gotu cola extract, cetearyl olivate, chlorophyll, orange oil, cocoyl proline, dicapryl ether, Disodium lauriminodipropionate tocopheryl phosphate (vitamin E phosphate), glycerin, glyceryl oleate, licorice extract, witch hazel extract, lactic acid, lecithin, lutein, macadamia seed oil, chamomile (chamomile) extract, evening primrose oil, olive leaf extract, rice bran oil, avocado oil, sewage extract, pomegranate sterol, resveratrol, rose oil, sandalwood oil, titanium dioxide, folic acid, glycerin, glyceryl linoleate [omega 6 (fatty acid vitamin F)], vitamin A palmitate, grape seed oil, halobetasol, adenosine, adenosine triphosphate, alpha hydroxane, allantoin, hyaluronic acid and derivatives, isoleutrol, tranexamic acid, glycolic acid, arginine, ascorbyl glucosamine, ascorbyl palmitate, salicylic acid, carnosic acid, alpha lipoic acid, gamma linolenic acid (GLA), panthenol, retinyl propionate, retinyl palmitate, furfuryl adenine, retinaldehyde, grippeptide, idebenone, dimethylaminoethanol (DMAE), niacinamide, beta-glucan, palmitoyl pentapeptide-4, palmitoyl oligopeptide/tetrapeptide-7, etosine, ceramide, phenylalanine, glucuronolactone, L-carnitine, hydroxyapatite, palmitoyl tripeptide-3, forskolin, zinc oxide, α-bisabolol, eugenol, silybin, soy isoflavone, catalpol, pseudoguaianolide derived from *Arnica chamissonis*, rosmarinic acid, rosmanol, silacylate, e.g. salicin, salicenin and salicylic acid, taraxasterol, α-lactocerol, isoleactoserol, taraxacoside, ceramide, arbutin, jingerol, shogaol, hypericin, elastin, collagen, and peptides thereof.

The bioactive substance may be included in an amount of 0.01 wt % to 50 wt %, specifically 0.1 wt % to 20 wt %, and more specifically 0.5 wt % to 10 wt % with respect to the total amount of a solvent. In addition, the core hydrogel may be included in an amount of 0.0001 wt % to 1 wt %, specifically 0.001 wt % to 0.1 wt %, and more specifically 0.005 wt % to 0.05 wt % with respect to the total amount of a solvent.

Multi-coated nanoparticles may include liposomes including a phospholipid bilayer. In addition, the liposome may be a nano liposome, a multi-layer liposome, an elastic liposome or an etosomal.

Elastic liposome means a liposome to which elasticity is imparted. Elastic liposomes are superior to other liposomes in elasticity. Therefore, the size may be freely changed. Elastic liposomes may contain various doses of hydrogels or bioactive substances.

Ethosome refers to a lipid structure prepared by mixing a phospholipid with ethanol. Ethosomes, due to the interaction of lipids and ethanol, may be particularly effective in permeating bioactive substances in the skin including some lipid layers.

Phospholipids constitute a double membrane, and may include natural phospholipids or synthetic lipids. Natural phospholipids may be at least one substance selected from a group of cholesterol, egg yolk lecithin (phosphatidylcholine), hydrogenated lecithin, soybean lecithin, lysolecithin, sphingomyelin, phosphatidylinositol, phosphatidic acid, phosphatidylethanolamine, phosphatidylserine, and phosphatidylserine. It may be one or more selected from the group consisting of phosphatidylinositol-4,5-diphosphoric acid, cardiolipin, and plasmarogen. In addition, the synthetic phospholipids are dicetylphosphate, distearoylphosphatidylcholine, dioleoylphosphatidylethanolamine, dipalmitoylphosphatidylcholine, dipalmitoylphosphatidylethanolamine, dipalmitoylphosphatidylserine, eleostearoylphosphatidylcholine, eleostearoylphosphatidylethanolamine and eleostearoylphosphatidylserine.

The bioactive substance may be mixed with the core hydrogel or may be combined with the core hydrogel to exist in the core layer as a hydrogel-bioactive substance complex. Nano-liposomes made of phospholipids surround the bioactive substance-hydrogel complex. Nano liposomes may be elastic liposomes, ethosomes, multi-layer liposomes or stealth liposomes.

The first coating layer is directly formed on the surface of the core layer. The first coating layer may be a substance to be surface-modified or coated by chitosan, which is a cationic hydrogel.

The amount of chitosan is 0.01 wt % to 5 wt %, 0.02 wt % to 2 wt %, 0.03 wt % to 1 wt %, 0.04 wt % to 0.9 wt %, 0.05 wt % to 0.5 wt %, 0.05 wt % to 0.3 wt %, 0.05 wt % to 0.4 wt %, or 0.05 wt % to 0.15 wt % with respect to the total weight of the multi-layer nanoparticles. In addition, the volume ratio of the core layer and the first layer may be 1:0.0001 to 1:10, 1:0.001 to 1:5, or 1:0.01 to 1:3.

Secondary coating is formed on the first coating layer. Secondary coating can be surface modified or coated with polyglutamic acid, which is an anionic hydrogel.

The amount of polyglutamic acid is 0.01 wt % to 5 wt %, 0.02 wt % to 2 wt %, 0.03 wt % to 1 wt %, 0.04 wt % to 0.9 wt %, 0.05 wt % to 0.5 wt %, 0.05 wt % to 0.3 wt %, 0.05 wt % to 0.4 wt %, or 0.05 wt % to 0.15 wt %. In addition, the volume ratio of the first layer and the second layer may be 1:0.0001 to 1:10, 1:0.001 to 1:5, or 1:0.01 to 1:3.

The third coating is formed on the secondary coating layer. The third coating can be surface modified or coated with chitosan.

The amount of chitosan of the third layer is 0.001 wt % to 0.5 wt %, 0.002 wt % to 0.2 wt %, 0.03 wt % to 0.1 wt %, 0.004 wt % to 0.009 wt %, 0.005 wt % with respect to the total weight of the multi-layer nanoparticles. % To 0.05 wt %, 0.005 wt % to 0.03 wt %, 0.005 wt % to 0.3 wt %, 0.005 wt % to 0.4 wt %, or 0.01 wt % to 0.15 wt %. In addition, the volume ratio of the second layer and the third layer may be 1:0.0001 to 1:1, 1:0.001, or 1:0.01.

If the amount of hydrogel is out of the above-described range, layers of the multi-coated nanoparticles may be separated, and then entrapment efficiency may be lowered.

In addition, when the amount of hydrogel is out of the above-described range, the binding ratio of the cationic hydrogel and the anionic hydrogel does not match. Accordingly, the multi-coated nanoparticles may not form an effective encapsulation structure and may have a non-uniform polydispersed form.

Multi-coated nanoparticles may include four or more coatings. The coating layer of nanoparticles may have a structure with alternating substances. For example, in the multi-coated nanoparticles, a chitosan coating layer may be positioned on the polyglutamic acid coating layer, and a polyglutamic acid coating layer may be positioned on the chitosan coating layer.

The multi-coated nanoparticle may further have a fourth coating layer made of polyglutamic acid. In addition, the multi-coated nanoparticles may further have a fifth coating layer made of chitosan.

The multi-coated nanoparticle may have an entrapment rate of 90% or more. For example, it may have an entrapment rate of 92% or more, 93% or more, 95% or more, and preferably 98% or more.

In the multi-coated nanoparticle, the cationic hydrogel of the first layer and the anionic hydrogel of the second layer are combined with each other. In addition, since the anionic hydrogel of the second layer forms a bond with the cationic hydrogel of the third layer, the stability and entrapment efficiency of the nanoparticles are high, and as a result, the bioactive substance can be sustained release.

The size of the multi-coated nanoparticle is 10 nm to 1000 nm, 10 nm to 500 nm, 10 nm to 300 nm, for example, 10 nm to 250 nm, 20 nm to 240 nm, 30 nm to 230 nm, 40 nm to 220 nm, 50 nm to 210 nm, 60 nm to 210 nm, 70 nm to 200 nm, 80 nm to 200 nm, 90 nm to 190 nm, 100 nm to 190 nm, or 100 nm to 180 nm.

If the size of the multi-coated nanoparticles is less than the above-described range, the drug cannot be properly encapsulated. In addition, if the size of the multi-coated nanoparticles exceeds the above-described numerical range, the multi-coated nanoparticles are not dispersed in a solution, so that the multi-coated nanoparticles may precipitate or deteriorate their stability.

The method for preparing multi-coated nanoparticles according to another embodiment of the present invention includes: i) providing a core layer for forming liposomes by mixing phospholipids in a solution including bioactive particles and a core hydrogel, ii) coating chitosan to the core layer, iii) coating polyglutamic acid on the first coating layer, and iv) coating chitosan on the second coating layer.

In the above-described method for preparing multi-coated nanoparticles, multi-coating, nano-particles, core layer, first coating, second coating, third coating, bioactive substance, core hydrogel, and phospholipid are the same as the described above multi-coated nanoparticles, its detailed description is omitted.

The step of forming the core layer includes: i) preparing a bioactive particle-hydrogel solution by mixing the bioactive particles and the core hydrogel; ii) preparing a phospholipid solution; and iii) forming a liposome of a phospholipid double membrane by mixing the bioactive particle-hydrogel solution and the phospholipid solution. The bioactive particles and the core hydrogel may have charges opposite to each other. Nanoparticles have a structure in which a core layer including a core hydrogel and a bioactive substance is entrapped by a phospholipid double layer. As a result, it is easy to entrap the hydrogel-bioactive substance complex, its stability increases, and the bioactive substance can be released slowly.

Step for forming the first coating may be surface-modified or coated by mixing chitosan in the core layer. The amount of chitosan is 0.01 wt % to 5 wt %, 0.02 wt % to 2 wt %, 0.03 wt % to 1 wt %, 0.04 wt % to 0.9 wt %, 0.05 wt % to 0.5 wt %, 0.05 wt % to 0.3 wt % or 0.05 wt % to 0.4 wt % with respect to the total weight of the multi-layer nanoparticles. In addition, the volume ratio of the core layer and the first layer may be 1:0.0001 to 1:10, 1:0.001 to 1:5, or 0.01 to 1:3.

In the step for forming the second coating, a coating layer may be formed on the first coating layer. Specifically, the nanoparticles may be surface-modified or coated by mixing polyglutamic acid. The polyglutamic acid amount is 0.01 wt % to 5 wt %, 0.02 wt % to 2 wt %, 0.03 wt % to 1, 0.04 wt % to 0.9 wt %, 0.05 wt % to 0.5 wt %, 0.05 wt % to 0.3 with respect to the total weight of the nanoparticles. It may be wt % or 0.05 wt % to 0.4 wt %. In addition, the volume ratio of the first layer and the second layer may be 1:0.0001 to 1:10, 1:0.001 to 1:5, or 0.01 to 1:3.

In the step for forming the third coating, a third coating layer may be formed on the second coating layer. Specifically, the nanoparticles may be surface-modified or coated by mixing chitosan. The amount of chitosan in the third layer is 0.001 wt % to 0.5 wt %, 0.002 wt % to 0.2 wt %, 0.03 wt % to 0.1 wt %, 0.004 wt % to 0.009 wt %, 0.005 wt % to 0.05 wt % with respect to the total weight of the nanoparticles %, 0.005 wt % to 0.03 wt %, 0.005 wt % to 0.3 wt %, or 0.005 wt % to 0.4 wt %. In addition, the volume ratio of the second layer and the third layer may be 1:0.0001 to 1:1, 1:0.001, or 1:0.01.

If the amount of chitosan in the third layer is out of the above-described range, layer of the nanoparticles may be separated, and the entrapment efficiency may decrease. In addition, if the amount of chitosan in the third layer is too low, the binding ratio of the cationic hydrogel and the anionic hydrogel does not match, so that the entrapping structure cannot be efficiently formed, and a non-uniform polydispersed form may be obtained.

The above-described method may include four or more coating steps.

The fourth coating layer of the nanoparticles may have a charge opposite to that of the third coating layer. For example, in nanoparticles, a polyglutamic acid coating layer may be positioned on the chitosan coating layer while a chitosan coating layer may be positioned on the polyglutamic acid coating layer.

The above-described method may further include a fourth coating step of coating polyglutamic acid after performing the third coating. In addition, it may further include a fifth coating step of coating chitosan after performing the fourth coating.

The above-described method may further include mixing purified water or alcohol with the coated nanoparticles. The above-described method can complete the coating of nano-liposomes, including these steps.

The above-described method may further comprise high pressure homogenizing the coated particles. The high-pressure homogenization may be performed under 10 bar to 5000 bar, and may be performed once to five times. For example, it may be performed once to 4 times, 2 to 4 times, or 1 to 3 times under 20 bar to 3000 bar, 30 bar to 2000 bar, 40 bar to 1500 bar, 50 bar to 1400 bar or 100 bar to 1300 bar. The above-described method enhances the stability of the multi-layer hydrogel structure since it includes a high-pressure homogenization step under specific conditions.

In the nanoparticles, the cationic hydrogel of the first layer and the anionic hydrogel of the second layer are combined with each other. The anionic hydrogel of the second layer is combined with the cationic hydrogel of the third layer, so that the nanoparticles have high stability and entrapment efficiency, and as a result, the drug can be sustained release.

The size of the multi-layer nanoparticles may be 10 nm to 1000 nm, 10 nm to 500 nm, 10 nm to 300 nm, for example, 10 nm to 250 nm, 20 nm to 240 nm, 30 nm to 230 nm, 40 nm to 220 nm, 50 nm to 210 nm, 60 nm to 210 nm, 70 nm to 200 nm, 80 nm to 200 nm, 90 nm to 190 nm, 100 nm to 190 nm or 100 nm to 180 nm.

If the size of the nanoparticles is too small, the drug cannot be properly entrapped. In addition, if the size of the nanoparticles is too large, the nanoparticles are not dispersed in the solution and thus precipitated, the stability of the particles is deteriorated, and then the definition of the nano-liposome may not be met.

The nanoparticles include a core layer including a hydrogel and bioactive particles, and a hydrogel multi-layer. As a result, nanoparticles are not only easy to be mass-produced, but also have a high entrapment rate and stability, so that bioactive particles can be continuously released for a long period of time.

DETAILED DESCRIPTION

Figure 1:
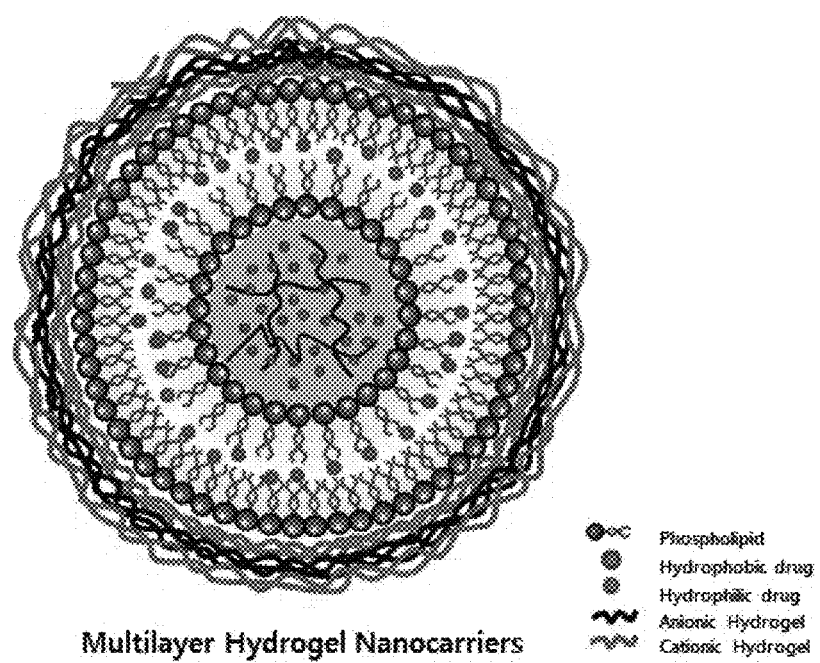
FIG. 1 is a schematic diagram of a multi-layered hydrogel nanoparticle including three coatings according to an embodiment of the present invention.

Embodiments of the present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

To clearly describe embodiments of the present invention, parts that are irrelevant to the description are omitted, and like numerals refer to like or similar constituent elements throughout the specification.

In addition, unless explicitly described to the contrary, the word "comprise" and variations such as "comprises" or "comprising" will be understood to imply the inclusion of stated elements but not the exclusion of any other elements.

Hereinafter, a chirp noise generation device and method for a compressed pulse signal according to an embodiment of the present invention will be described with reference to FIG. 1 to FIG. 6.

Embodiment 1. Preparation of Experimental and Comparative Groups of Nanoparticles

1.1. Setting Experimental Examples and Comparative Examples

In order to confirm a difference in the effect of each of the coating stages and amounts of the nanoparticles, nanoparticles with the first coating of Experimental Example 1, nanoparticles with the second coating of Experimental Example 2, nanoparticles with the third coating of Experimental Example 3, uncoated nanoparticles of Experimental Example 4, and no hydrogel was added to the core of Experimental Example 5 were used.

In addition, as shown in Table 1, in order to compare the effect of the nanoparticles for each amount of hydrogel, Comparative Example 1 and Comparative Example 2 were set by varying the amount of compositions in each coating layer.

Table 1 shows the coating and amount of compositions according to the Experimental and Comparative examples.

TABLE 1

| Nano particle Structure | | Coating layer (wt %) | | | | | hydrogel (wt %) | |
|---|---|---|---|---|---|---|---|---|
| | | Experimental Example 1 | Experimental Example 2 | Experimental Example 3 | Experimental Example 4 | Experimental Example 5 | Comparative Example 1 | Comparative Example 2 |
| Core | Peptide | 0.05% | 0.05% | 0.05% | 0.05% | 0.05% | 0.05 | 0.05 |
| | Hydrogel | 0.005% | 0.005% | 0.005% | 0.005% | — | 0.005% | 0.005% |
| Liposome | Phospholipid | 2.0% | 2.0% | 2.0% | 2.0% | 2.0% | 2.0% | 2.0% |
| Coating agent | Chitosan | 0.1% | 0.1% | 0.1% | — | 0.1% | 0.1% | 0.1% |
| | Poly Glutamic acid | — | 0.1% | 0.1% | — | 0.1% | 0.1% | 0.05% |
| | Chitosan | — | — | 0.01% | — | 0.01% | 0.15% | 0.01% |

1.2. Preparation of Uncoated Nano Liposome (Experimental Example 4)

In order to prepare uncoated nanoparticles, a peptide-hydrogel solution and a phospholipid solution were prepared.

The peptide-hydrogel solution was prepared by adding and dissolving Copper TriPeptide-1 (CTP) and polyglutamic acid in purified water. The bioactive substance was adjusted to 0.05 wt % and the polyglutamic acid of the core layer was adjusted to 0.005 wt % with respect to the total weight of the nanoparticle solution.

Phospholipid solution was prepared by dissolving hydrogenated lecithin in ethanol. More specifically, ethanol was prepared in 10 wt % and hydrogenated lecithin was prepared in 2.0 wt % with respect to the total amount of the nanoparticle solution.

The peptide-hydrogel solution was mixed with the phospholipid solution and was stirred to prepare a core-phospholipid mixed solution. 10.0 wt % of purified water was added to the core-phospholipid mixed solution and was stirred to form a double-layered nanoparticle. Then, purified water was added to be 70.0 wt % of the total amount of nanoparticle solution and was stirred to remove ethanol through a degassing process. Finally, the solution was gradually cooled to room temperature and stirred to prepare nanoparticles of Experimental Example 4 in which there was no coating layer and the peptide was entrapped.

1.3. Preparation of Primary Coated Nano-Liposome (Experimental Example 1)

Nanoparticles with a positive first coating of Experimental Example 1 having an amount of composition shown in Table 1 was prepared.

More specifically, 1.0 wt % chitosan aqueous solution was prepared by dissolving chitosan, which is a cationic hydrogel, in purified water, and was added to the nanoparticles of Example 1.2 for first coating. Next, purified water was further added so that the amount thereof became 100%, thereby the primary coated nanoparticles of Experimental Example 1 was prepared.

1.4. Preparation of Secondary Coated Nano-Liposome (Experimental Example 2)

Nanoparticles with a positive second coating of Experimental Example 2 having an amount of composition shown in Table 1 was prepared.

More specifically, 1 wt % polyglutamic acid aqueous solution was added to the primary coated nanoparticles of Example 1.3, thereby the second coated nanoparticles of Experimental Example 2 were prepared.

1.5. Preparation of Third Coated Nano Liposome (Experimental Example 3)

Nanoparticles of Experimental Example 3 coated with the amount of composition shown in Table 1 were prepared.

A 0.1 wt % chitosan aqueous solution was prepared and added to the secondary coated nano-liposome of Example 1.4, followed by being thirdly coated. The coated nanoparticles were homogenized under high pressure through a microfluidizer. Specifically, the pressure of the high-pressure homogenization was set to 1000 bar, and the number of passes was set to 3 times.

Figure 2:
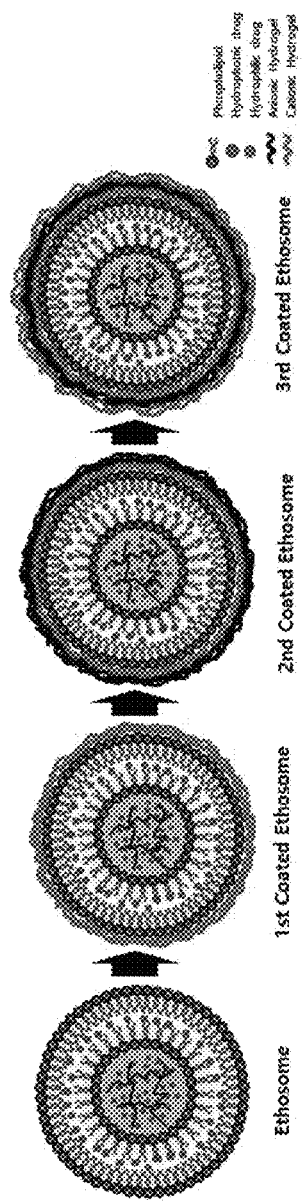
FIG. 2 is a diagram schematically showing a coating process of multilayed hydrogel nanoparticles according to an embodiment of the present invention.

FIG. 1 is a schematic diagram of nanoparticles including a hydrogel according to an embodiment of the present invention and FIG. 2 is a schematic diagram showing a coating process of nanoparticles including a hydrogel according to an embodiment of the present invention.

As shown in FIGS. 1 and 2, the nanoparticle of Experimental Example 3 includes the core layer containing a hydrogel-bioactive substance and a hydrogel multi-layer coated on the core layer. Therefore, it was confirmed that the drug entrapment rate is high and a sustained-release effect appears.

1.6. Preparation of Thirdly Coated Nano-Liposome without Core Hydrogel (Experimental Example 5)

Nanoparticles of Experimental Example 5 were prepared with a third coating of the amount shown in Table 1 without the addition of the core hydrogel.

The peptide-hydrogel solution entrapped in the core of Example 1.2 was not prepared, and only an aqueous peptide solution was provided to prepare a core-phospholipid solution. Then, it was prepared in the same manner as the that of third coated nano-liposome.

1.7. Preparation of Third-Coated Nano-Liposomes (Comparative Examples 1 and 2) with Different Amounts of Compositions Nanoparticles of Comparative Examples 1 and 2 were third coated in the amount of the compositions shown in Table 1 above.

Comparative Example 1 was prepared in the same manner, except that 0.15 wt % chitosan aqueous solution was prepared and added to the second coated nano-liposome of Experimental Example 2 to perform the third coating.

Comparative Example 2 was prepared in the same manner, except that the primary coated nanoparticles of Experimental Example 1 were secondarily coated by adding a 0.05 wt % polyglutamic acid aqueous solution.

Embodiment 2. Comparison of Particle Size, Zeta Potential, and Stability According to Coating Steps of Nanoparticles and Amount of Hydrogel

2.1. Comparison of Particle Size and Zeta Potential of Nanoparticles by Amount In order to compare the particle size and zeta potential of the nanoparticles according to the coating layer structure and the amount of hydrogel, the size and zeta potential of the nanoparticles of Embodiment 1 were measured using a nanoparticle analyzer. Zeta potential refers to the electrostatic potential of the cross section of particles, and is a numerical value of the degree of attraction or repulsion between adjacent particles. If the zeta potential is equal to or less than 0.3, the nanoparticles exist in a stable monodisperse form.

Figure 3:
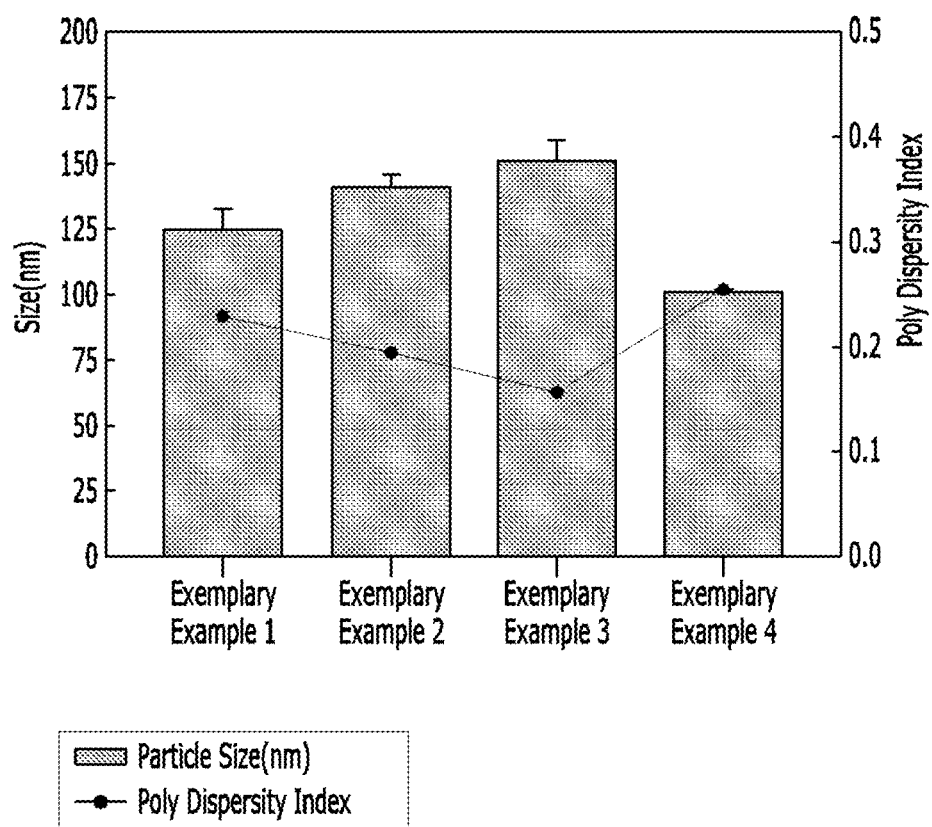
FIG. 3 is a graph showing the analysis of the size and polydispersity index of multi-layered hydrogel nanoparticles in each coating step.

Table 2 is a graph showing the particle size and zeta potential of nanoparticles according to the coating layer structure and amount of hydrogel. FIG. 3 is a graph showing a particle size and zeta potential analysis of nanoparticles according to a coating step and amount of hydrogel.

TABLE 2

| | Experimental Example 1 | Experimental Example 2 | Experimental Example 3 | Experimental Example 4 | Experimental Example 5 | Comparative Example 1 | Comparative Example 2 |
|---|---|---|---|---|---|---|---|
| Particle size (nm) | 134.31 ± 3.57 | 142.69 ± 3.06 | 153.91 ± 4.48 | 106.95 ± 5.06 | 157.45 ± 0.79 | 2265.98 ± 316.9 | 2221.66 ± 418.7 |
| Poly Dispersity index | 0.229 | 0.194 | 0.157 | 0.254 | 0.154 | 0.713 | 0.427 |

TABLE 2-continued

| | Experimental Example 1 | Experimental Example 2 | Experimental Example 3 | Experimental Example 4 | Experimental Example 5 | Comparative Example 1 | Comparative Example 2 |
|---|---|---|---|---|---|---|---|
| Zete Potential (mV) | 29.07 ± 2.24 | −43.26 ± 2.01 | −38.51 ± 0.82 | −40.98 ± 2.3 | −37.63 ± 1.35 | 17.86 ± 0.28 | −15.13 ± 0.92 |

Figure 4:
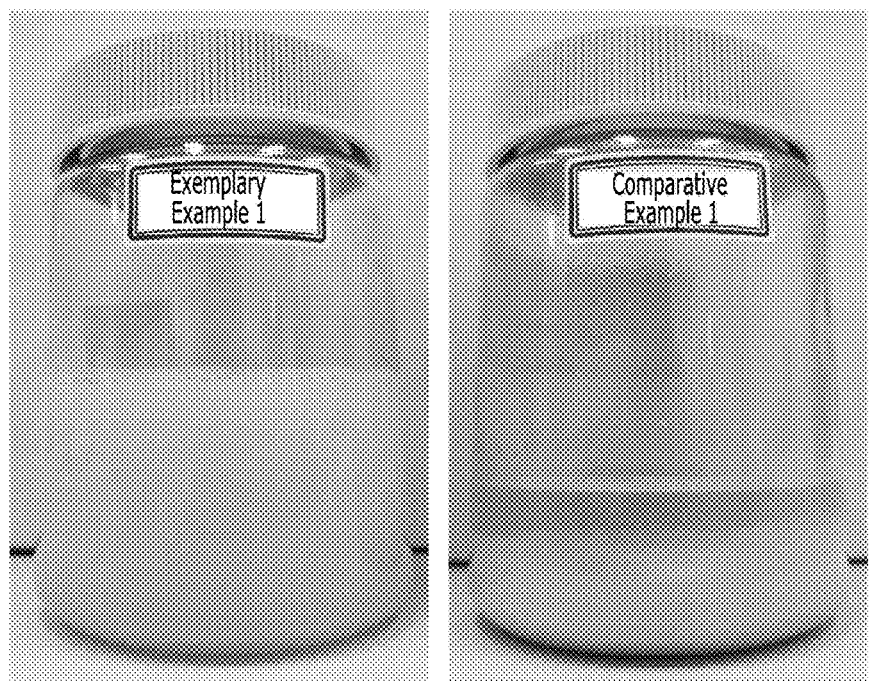
FIG. 4 is a diagram showing the long-term stability of the composition 30 days after preparation of the composition according to Experimental Example 1 and Comparative Example 1.

As shown in Table 2 and FIG. 3, the average size of the nanoparticles without coating hydrogel in Experimental Example 4 was 106.95±5.06 nm. However, in Experimental Examples 1 to 3 in which the hydrogel was coated once, twice, and third times, the size of nanoparticle size gradually FIG. 4 is a photograph of a sample measuring the long-term stability of nanoparticles after 30 days of Experimental Example 1 and Comparative Example 1. In FIG. 4, Experimental Example 1 is denoted by (A), and Comparative Example 1 is denoted by (B).

TABLE 3

| | Experimental Example 1 | Experimental Example 2 | Experimental Example 3 | Experimental Example 4 | Experimental Example 5 | Comparative Example 1 | Comparative Example 2 |
|---|---|---|---|---|---|---|---|
| 1 day | Stable | Stable | Stable | Stable | Stable | Stable | Stable |
| 5 day3 | Stable | Stable | Stable | Stable | Stable | Precipitated | Precipitated |
| 10 day3 | Stable | Stable | Stable | Stable | Stable | Layer Separated | Layer Separated |
| 20 day3 | Stable | Stable | Stable | Stable | Stable | Layer Separated | Layer Separated |
| 30 day3 | Stable | Stable | Stable | Stable | Agglomerated | Layer Separated | Layer Separated | increased as the nanoparticles included more multiple coating layers.

In addition, although nanoparticles were formed in Comparative Example 1 and Comparative Example 2, the binding ratio between chitosan and polyglutamic acid did not match, so it could be confirmed that chitosan and polyglutamic acid form a complex through self-assembly to be polydispersed.

However, the nanoparticles of Experimental Example 3 had a size of 153.91±4.48 nm, and the PDI was also 0.3 or less, indicating that they were monodispersed. These results imply that the third-coated nanoparticles of Experimental Example 4 were more stable than those of Experimental Examples 1 to 3.

In addition, in the Experimental Example 4, the zeta potential of the nanoparticles was −40.98±2.3 mV, but it was confirmed that the zeta potential of the nanoparticles in Experimental Example 1 was changed to 29.07±2.24 mV. This change in the zeta potential means that an electrostatic bond is formed between the cationic hydrogel and the anionic hydrogel during hydrogel coating.

2.2. Comparison of Long-Term Stability of Nanoparticles

In order to compare the long-term stability of the nanoparticles according to the structure of the coating layer and the amount of hydrogel, the long-term dispersion stability of the nanoparticles in Experimental Examples 1 to 5 and Comparative Examples 1 to 2 was measured.

Specifically, each nanoparticle solution was placed in a constant temperature chamber of 45° C., and changes in shape were observed with the naked eye after 1, 5, 10, 20, and 30 days. The change in shape was evaluated by discoloration and layer separation over time.

Table 3 shows the long-term stability of nanoparticles according to the coating layer structure and amount of hydrogel.

As a result, as shown in Table 3, it was confirmed that the nanoparticles of Experimental Examples 1 to 4 had excellent dispersion stability even without a surfactant. In particular, in the nanoparticles of Experimental Example 5 in which the hydrogel was not included in the core, aggregation of the particles was confirmed after 30 days. Among the nanoparticles of Comparative Example 1 and Comparative Example 2, a layer was separated by sinking of particles. Therefore, it was confirmed that the stability of the nanoparticles was very low. These results mean that the long-term stability of the nanoparticles varies depending on whether the core hydrogels or coating layers exist or not, the number of coating layers, and the amount of the hydrogel.

2.3. Comparison of Entrapment Efficiency of Experimental Examples 1 to 5 Nano-Liposomes The entrapment efficiency of the bioactive component was measured using the nanoparticles of Experimental Examples 1 to 5.

First, a bioactive substance that was not entrapped from the nanoparticle solution was separated using an MWCO bag (Molecular weight cut-off 10,000 dalton, Amicon). Next, the entrapment rate of each nanoparticle was calculated using Equation 1 below.

$$EE_{Free} = (W_{Total} - W_{Free})/W_{Total} \times 100 \quad \text{[Equation 1]}$$

In Equation 1, $EE_{Free}$ is the entrapment efficiency of the bioactive substance encapsulated in the multi-layer hydrogel nanoliposome, $W_{Total}$ is the total concentration of the added bioactive substance, and $W_{Free}$ is the concentration of the bioactive substance not entrapped in the multi-layered hydrogel nanoparticles.

Table 4 is a table showing the calculation results of the entrapment rate of each nanoparticle.

TABLE 4

|  | Experimental Example 1 | Experimental Example 2 | Experimental Example 3 | Experimental Example 4 | Experimental Example 5 |
|---|---|---|---|---|---|
| Entrapment Efficiency (%) | 93.46 | 97.86 | 99.56 | 83.57 | 91.5 |

As a result, as shown in Table 4 and FIG. 4, the entrapment rate of the nanoparticles of Experimental Example 4 without hydrogel coating was as low as 83.57%, and the entrapment rate increased as the number of coating layer increased. Thus, the nanoparticles of Experimental Example 3 had the highest entrapment rate. In addition, the nanoparticles of Experimental Example 5 to which the hydrogel was not added to the core exhibited a relatively low entrapment efficiency. This result means that the binding force of the double layer of the nanoparticles multi-coated with the hydrogel of opposite charges is strengthened, so that the entrapment rate of the bioactive substance is high.

2.4. Comparison of Sustained-Release Effects of Experimental Examples 1 to 4 Nanoparticles Using the nanoparticles of Experimental Examples 1 to 4, the amount of drug release in vitro of the bioactive ingredient was measured.

Specifically, 4 ml of the nanoparticle solutions of Experimental Examples 1 to 4 and 44 ml of a phosphate buffer of pH 7.4 were placed in a dialysis bag (molecular weight cut-off approximately 10,000 dalton, Thermal) and stirred by 200 RPM at 37° C. Next, 1 ml of samples were taken after 1, 2, 4, 6, 24, 48, 72 and 96 hours from the stirred solution, and the same amount of buffer solution was refilled. The collected samples were quantitatively analyzed by high performance liquid chromatography (HPLC) to measure the released bioactive substances over time.

Table 5 shows the amount of bioactive substances released by the nanoparticles extracted for each time period.

Figure 5:
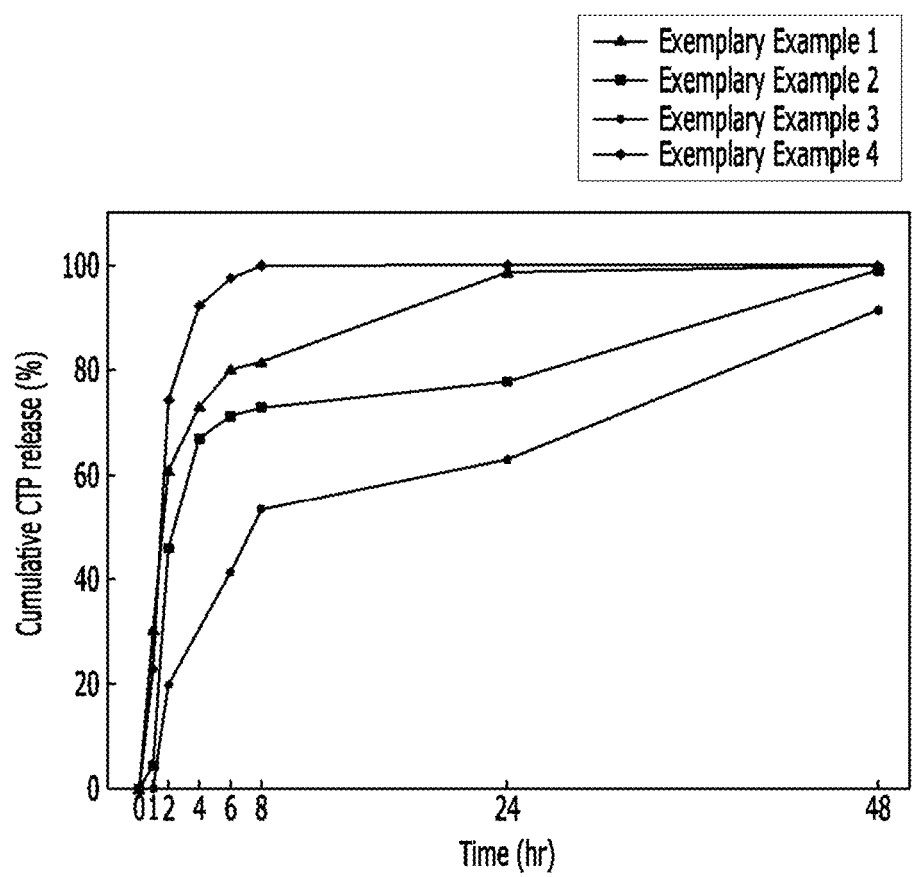
FIG. 5 is a graph showing the sustained-release behavior over time of nanoparticles including a hydrogel according to an embodiment of the present invention.

FIG. 5 is a graph showing the sustained-release behavior over time of nanoparticles including a hydrogel according to an embodiment of the present invention.

TABLE 5

| Cumulative release (%) | Experimental Example 1 | Experimental Example 2 | Experimental Example 3 | Experimental Example 4 |
|---|---|---|---|---|
| 1 hr | 30.04 | 4.45 | 0.00 | 23.11 |
| 2 hr | 60.80 | 45.98 | 19.60 | 74.14 |
| 4 hr | 72.81 | 66.90 | 37.64 | 92.30 |
| 6 hr | 79.80 | 71.30 | 41.20 | 97.60 |
| 8 hr | 81.40 | 72.82 | 53.30 | 100.00 |
| 24 hr | 98.60 | 77.83 | 62.84 | 100.00 |
| 48 hr | 100.00 | 98.91 | 91.17 | 100.00 |

As a result, as shown in Table 5 and FIG. 5, it was confirmed that most of the bioactive substances were released from the uncoated nanoparticles of Experimental Example 4 after 4 hours.

On the contrary, in the multi-layered nanoparticles of Experimental Examples 1 to 3, it was confirmed that initial release was suppressed and a sustained release behavior was shown. In particular, in the Experimental Example 3, it was confirmed that only 40% of the bioactive substance was released from the nanoparticles even after 6 hours. These results indicate that the nanoparticles have excellent entrapment efficiency and stability of the bioactive substance, and that the nanoparticles have a sustained-release behavior through inhibition of initial release.

Embodiment 3. Preparation of Experimental Group of Nanoparticles Encapsulating Natural Extracts

3.1. Preparation of Nanoparticles Encapsulating Natural Extracts and Coating by Step In order to check the difference in shape according to the bioactive substances encapsulated in the nanoparticles, nanoparticles subjected to first coating by encapsulating natural extracts from existing peptides were set as Experimental Example 6, and nanoparticles subjected to be coated twice were set as Experimental Example 7, and the nanoparticles subjected to be coated three times were set as Experimental Example 8. Uncoated nanoparticles were set as Experimental Example 9.

Table 6 shows the amount of compositions for coatings used in the experiment.

TABLE 6

| Nano particle Structure | | Experimental Example 6 | Experimental Example 7 | Experimental Example 8 | Experimental Example 9 |
|---|---|---|---|---|---|
| Core | Natural extracts | 0.05% | 0.05% | 0.05% | 0.05% |
|  | Hydrogel | 0.005% | 0.005% | 0.005% | 0.005% |
| Liposome | Phospholipid | 2.0% | 2.0% | 2.0% | 2.0% |
| Coating agent | Chitosan | 0.1% | 0.1% | 0.1% | — |
|  | Poly Glutamic acid | — | 0.1% | 0.1% | — |
|  | Chitosan | — | — | 0.01% | — |

3.2. Preparation of Uncoated Nano Liposome (Experimental Example 9)

In order to prepare uncoated natural extract-encapsulated nanoparticles, a natural extract-hydrogel solution and a phospholipid solution were prepared and mixed to provide a core-phospholipid mixed solution.

Natural extract-hydrogel solution was prepared by adding natural extracts, *Pinus rigida* Bark Extract, and polyglutamic acid to purified water and then dissolving them.

The following process was performed in the same manner as the process of manufacturing the uncoated nanoparticles of Experimental Example 4 shown in Example 1.2, and the nanoparticles of Experimental Example 9 in which the natural extract was encapsulated were prepared.

3.3 Preparation of Primary Coated Nano-Liposome (Experimental Example 6)

Nanoparticles of Experimental Example 6 coated with the amount shown in Table 6 were prepared.

Specifically, 1.0 wt % chitosan aqueous solution was prepared by dissolving chitosan, which is a cationic hydrogel, in purified water. Then, the chitosan aqueous solution was added to the nanoparticles of Example 3.2 for primary coating. Next, purified water was added for the total amount to be 100% to prepare the primary coated nanoparticles of Experimental Example 6.

3.4. Preparation of Secondary Coated Nano Liposome (Experimental Example 7)

Nanoparticles of Experimental Example 7 coated with the amount shown in Table 6 were prepared.

Specifically, to the primary coated nanoparticles of Example 3.3, 1 wt % polyglutamic acid aqueous solution was added to prepare the second coated nanoparticles of Experimental Example 7.

3.5. Preparation of Third Coated Nano Liposome (Experimental Example 8)

The nanoparticles of Experimental Example 8 coated with the amount shown in Table 6 were prepared.

A 0.1 wt % chitosan aqueous solution was prepared and added to the second coated nano-liposome of Example 3.4 to prepare the nanoparticles of Experimental Example 8 for the third coating. The coated nanoparticles were homogenized under high pressure through a microfluidizer. Specifically, the pressure condition of the high-pressure homogeneous step was set to 1000 bar, and the number of passes was set to 3 times.

Embodiment 4. Comparison of a Particle Size and Zeta Potential of the Nanoparticles According to by Coating Step and Amount of Hydrogel

4.1 Comparison of Particle Size and Zeta Potential of Nanoparticles by Amount In order to compare the particle size and zeta potential of the nanoparticles according to the coating layer structure and the amount of hydrogel, the size and zeta potential of the nanoparticles encapsulated with the natural extract and the coated nanoparticles of Exemplary Example 3 were measured using a particle size analyzer.

Table 7 is a graph showing the particle size and zeta potential of nanoparticles according to the coating layer structure and amount of hydrogel.

TABLE 7

|  | Experimental Example 6 | Experimental Example 7 | Experimental Example 8 | Experimental Example 9 |
| --- | --- | --- | --- | --- |
| Particle size (nm) | 125.94 ± 6.48 | 165.70 ± 06.05 | 177.83 ± 05.46 | 130.88 ± 00.48 |
| Poly Dispersity index | 0.243 | 0.225 | 0.201 | 0.275 |
| Zete Potential (mV) | 28.16 ± 01.76 | −44.43 ± 01.66 | −42.00 ± 00.87 | −39.90 ± 04.17 |

As shown in Tables 2 and 7, in the nanoparticles in which a bioactive substance was encapsulated in the core with a peptide of Experimental Example 4, the particle size was 106.95±5.06 nm. In contrast, the nanoparticles of Experimental Example 9 encapsulating natural extracts having various components increased in size of 130.88±0.48 nm due to the encapsulated components. The size of the hydrogel coating gradually increased as it included the multiple coating layers of the nanoparticles of Experimental Examples 6 to 8 in which the first, second, and third coating were performed, respectively.

4.2 Comparison of Entrapment Efficiency of Nano-Liposomes of Experimental Examples 6 to 9

Using the nanoparticles of Experimental Examples 6 to 9, the entrapment efficiency of Catechin among various components of the natural extract was measured. Analysis was carried out in the same manner as in Example 2.3.

Table 8 is a table showing the results of calculating the entrapment rate for each nanoparticle.

TABLE 8

|  | Experimental Example 6 | Experimental Example 7 | Experimental Example 8 | Experimental Example 9 |
| --- | --- | --- | --- | --- |
| Entrapment Efficiency (%) | 89.3 | 90.6 | 94.9 | 67.5 |

As shown in Table 8, it was confirmed that the entrapment rate of the nanoparticles of Experimental Example 9 in which the hydrogel was not coated was 67.5%. However, as the coating layer increased, the entrapment rate increased, and thus the entrapment rate of the nanoparticles of Experimental Example 8 was the highest and the remarkable effect was exhibited. These results mean that in the nanoparticles coated with a multi-layered hydrogel of opposite charges, the binding force of the double coating layer is strengthened, so that the entrapment rate of the bioactive substance is high.

4.3 Measurement of DPPH Radical Scavenging Ability of Nanoparticles by Time DPPH radical scavenging ability was measured to confirm the effect of antioxidant physiological activity according to the sustained-release release of nanoparticles according to the coating layer structure and amount of hydrogel.

50 μL of 0.2 mM 1,1-diphenyl-2-picrylhydrazyl (DPPH) was added to 100 ul of each sample solution. Then, it was stirred and reacted at room temperature for 30 minutes, and then the ELISA reader (Powerwave XS2, Biotek, USA) was used to measure the absorbance at 571 nm. The control groups were Butylated Hydroxynisole (BHA) and Catechin.

Next, using Equation 2 below, the DPPH radical scavenging ability of each nanoparticle was calculated.

DPPH radical scavenging ability (%)=(1−absorbance of sample added group/absorbance of no added group)×100  [Equation 2]

Table 9 shows the results of DPPH radical scavenging activity of Experimental Examples 6 to 9 and BHA and Catechin over time.

Figure 6:
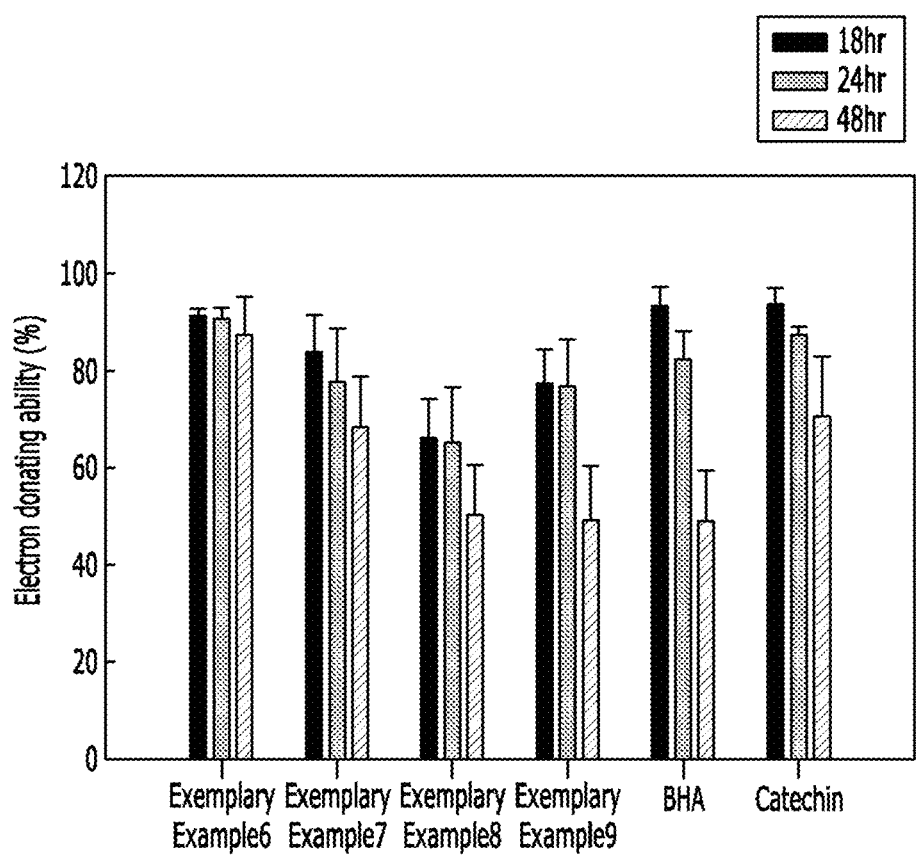
FIG. 6 is a graph showing DPPH radical scavenging activity over time of a multi-layer liposome according to an embodiment of the present invention.

FIG. 6 is a graph showing DPPH radical scavenging activity over time of a multi-layer liposome according to an embodiment of the present invention.

TABLE 9

|  | Experimental Example 6 | Experimental Example 7 | Experimental Example 8 | Experimental Example 9 | BHA | Catechin |
|---|---|---|---|---|---|---|
| 18 hr | 91.0042 | 83.6820 | 66.1088 | 77.1967 | 93.2084 | 93.4211 |
| 24 hr | 90.5882 | 77.6471 | 65.4118 | 76.7059 | 82.3362 | 87.4680 |
| 48 hr | 87.4016 | 68.5039 | 50.3937 | 49.2126 | 47.0031 | 70.5607 |

As shown in Table 9 and FIG. 7, DPPH radical scavenging ability was not significantly reduced in Experimental Example 6, which proceeded to the third coating, as shown as 91.0042% at 18 hours and 87.4016% at 48 hours. However, in the case of BHA and Catechin, which were used as controls, 93.2084% and 93.4211%, respectively, were identified after 18 hours, but rapidly decreased to 47.0031% and 70.5607% after 48 hours. This result means that the antioxidation effect component in the hydrogel-coated nanoparticles is continuously released for a long period of time to exhibit a sustained-release effect.

While embodiments of the present invention have been particularly shown and described with reference to the accompanying drawings, the specific terms used herein are only for the purpose of describing the invention and are not intended to define the meanings thereof or be limiting of the scope of the invention set forth in the claims. Therefore, a person of ordinary skill in the art will understand that various modifications and other equivalent embodiments of the present invention are possible. Consequently, the true technical protective scope of the present invention must be determined based on the technical spirit of the appended claims.

What is claimed is:

1. A multi-coated nanoparticle comprising:
a liposome core layer comprising a bioactive particle and a core hydrogel having a charge opposite to a charge of the bioactive particle, the liposome core layer that is surrounded by a phospholipid bilayer;
a first coating layer consisting of chitosan of 0.05 wt % to 0.15 wt % with respect to a total weight of the nanoparticle, the first coating layer located on the core layer;
a second coating layer consisting of polyglutamic acid of 0.06 wt % to 0.15 wt % with respect to the total weight of the nanoparticle, the second coating layer located on the first coating layer; and
a third coating layer consisting of chitosan of 0.005 wt % to 0.03 wt % with respect to the total weight of the nanoparticle, the third coating layer located on the second coating layer,
wherein the volume ratio of the first coating layer and the second coating layer is 1:0.0001 to 1:10, and wherein a size of the multi-coated nanoparticle is about 150 nm to 400 nm.

2. The multi-coated nanoparticle of claim 1, wherein the bioactive particle is at least one substance selected from a group of peptides, natural extracts, and vitamins.

3. The multi-coated nanoparticle of claim 1, wherein the core hydrogel is at least one substance selected from a group of hyaluronic acid, alginate, pectin, carrageenan, dextran sulfate, guar gum, gum arabic, xanthan gum, polyacrylic acid, polygalaturonic acid, carboxymethylcellulose, polyglutamic acid, agar, collagen peptide, starch, hydrolyzed starch, crosslinked starch, modified starch, dextrin, gamma polyglutamic acid, gelatin, alginic acid, and chitosan.

4. The multi-coated nanoparticle of claim 1, wherein the bioactive particle is mixed with the core hydrogel or combined with the core hydrogel to exist in the core layer as a hydrogel-bioactive substance complex and wherein the multi-coated nanoparticle is configured to release the bioactive particle in a sustained-release manner.

5. The multi-coated nanoparticle of claim 1, wherein the liposome core layer is a nano-liposome, a multi-layer liposome, an elastic liposome or an ethosome.

6. The multi-coated nanoparticle of claim 1, wherein the volume ratio of the core layer and the first coating layer is 1:0.0001 to 1:10.

7. A composition for skin care comprising:
multi-coated nanoparticles; and
purified water that is configured to contain the multi-coated nanoparticles; and wherein at least one of the multi-coated nanoparticles comprises:
a liposome core layer comprising a bioactive particle and a core hydrogel, the liposome core layer that is surrounded by a phospholipid bilayer;
a first coating layer consisting of chitosan of 0.05 wt % to 0.15 wt % with respect to a total weight of the nanoparticle;
a second coating layer consisting of polyglutamic acid of 0.06 wt % to 0.15 wt % with respect to the total weight of the nanoparticle;
a third coating layer consisting of chitosan of 0.005 wt % to 0.03 wt % with respect to the total weight of the nanoparticle, and
wherein the core hydrogel is configured to electrostatically bind to the bioactive particle,
wherein the volume ratio of the first coating layer and the second coating layer is 1:0.0001 to 1:10, and
wherein a size of the multi-coated nanoparticle is 150 nm to 400 nm.

8. The composition for skin care of claim 7, wherein the core hydrogel having a charge opposite to a charge of the bioactive particle.

9. The composition for skin care of claim 7, wherein the bioactive particle is at least one substance selected from a group of peptides, natural extracts, and vitamins.

10. The composition for skin care of claim 7, wherein an amount of the bioactive particle is 0.01 wt % to 50 wt % with respect to total weight of the composition.

11. The composition for skin care of claim 7, wherein an amount of the core hydrogel is 0.0001 wt % to 1 wt % with respect to total weight of the composition.

12. The composition for skin care of claim 7, wherein the core hydrogel is at least one substance selected from a group of hyaluronic acid, alginate, pectin, carrageenan, dextran sulfate, guar gum, gum arabic, xanthan gum, polyacrylic acid, polygalaturonic acid, carboxymethylcellulose, polyglutamic acid, agar, collagen peptide, starch, hydrolyzed starch, crosslinked starch, modified starch, dextrin, gamma polyglutamic acid, gelatin, alginic acid, and chitosan.

\* \* \* \* \*